(12) United States Patent
Kiss

(10) Patent No.: US 9,458,099 B2
(45) Date of Patent: Oct. 4, 2016

(54) METHOD OF MANUFACTURING UREA FROM REFUSE, PREFERABLY DOMESTIC WASTE, OF ANY COMPOSITION

(71) Applicant: THERMOSELECT Aktiengesellschaft, Triesenberg (LI)

(72) Inventor: Guenter Hans Kiss, Locarno (CH)

(73) Assignee: Thermoselect Aktiengesellschaft, Triesenberg (LI)

( * ) Notice: Subject to any disclaimer, the term of this patent is extended or adjusted under 35 U.S.C. 154(b) by 0 days.

(21) Appl. No.: 13/950,347

(22) Filed: Jul. 25, 2013

(65) Prior Publication Data

US 2015/0031916 A1    Jan. 29, 2015

(51) Int. Cl.
| | |
|---|---|
| *C07C 273/10* | (2006.01) |
| *C01B 3/02* | (2006.01) |
| *C01B 3/16* | (2006.01) |
| *C05F 9/00* | (2006.01) |
| *C10J 3/00* | (2006.01) |
| *C05C 9/00* | (2006.01) |
| *C10K 3/04* | (2006.01) |

(52) U.S. Cl.
CPC ............. *C07C 273/10* (2013.01); *C01B 3/025* (2013.01); *C01B 3/16* (2013.01); *C05C 9/00* (2013.01); *C05F 9/00* (2013.01); *C10J 3/00* (2013.01); *C10K 3/04* (2013.01); *C01B 2203/0283* (2013.01); *C01B 2203/068* (2013.01); *C10J 2300/0946* (2013.01); *C10J 2300/1668* (2013.01); *C10J 2300/1678* (2013.01)

(58) Field of Classification Search
CPC .................................................... C07C 273/10
USPC .......................................................... 564/69
See application file for complete search history.

(56) References Cited

U.S. PATENT DOCUMENTS

| 5,711,924 A | 1/1998 | Kiss |
| 6,448,441 B1 * | 9/2002 | Wing-Chiu et al. ............ 564/67 |
| 6,455,011 B1 | 9/2002 | Fujimura et al. |
| 2006/0228284 A1 | 10/2006 | Schmidt |

FOREIGN PATENT DOCUMENTS

| CA | 2347106 A1 | 11/2002 | |
| CN | 1143982 C | 3/2004 | |
| CN | 101407326 A | 4/2009 | |
| CN | 101506335 A | 8/2009 | |
| JP | 2008106117 | * 5/2008 | ...... C10J 2300/1634 |
| WO | 02/090250 A1 | 11/2002 | |
| WO | 2011/021944 A1 | 2/2011 | |

OTHER PUBLICATIONS

English Translation of JP2008106117, May 8, 2008, pp. 1-20.*
Higman and Burgt; "Gasification", 2003, Elsevier, Burlington, MA, USA, pp. 9, 231-238, 293-295.

* cited by examiner

*Primary Examiner* — Paul A Zucker
*Assistant Examiner* — Mark Luderer
(74) *Attorney, Agent, or Firm* — Marshall & Melhorn, LLC

(57) ABSTRACT

The invention relates to a method of manufacturing urea as a nitrogen-rich synthetic fertilizer from refuse of any composition, preferably from domestic waste. The organic waste components are first turned into gas in a high-temperature reactor with oxygen ($O_2$) which has been obtained in a cryogenic air separation plant. A synthesis gas arises which predominantly comprises carbon monoxide (CO), hydrogen ($H_2$) and carbon dioxide ($CO_2$). The carbon monoxide (CO) contained in the synthesis gas is subsequently converted with steam into hydrogen ($H_2$) and carbon dioxide ($CO_2$). The hydrogen is subsequently separated and is used for ammonia synthesis together with the elementary nitrogen ($N_2$) which arises as a by-product in cryogenic air separation. In the last process step, urea ($CO(NH_2)_2$) is manufactured from ammonia ($NH_3$) and the further synthesis gas component carbon dioxide ($CO_2$).

1 Claim, 1 Drawing Sheet

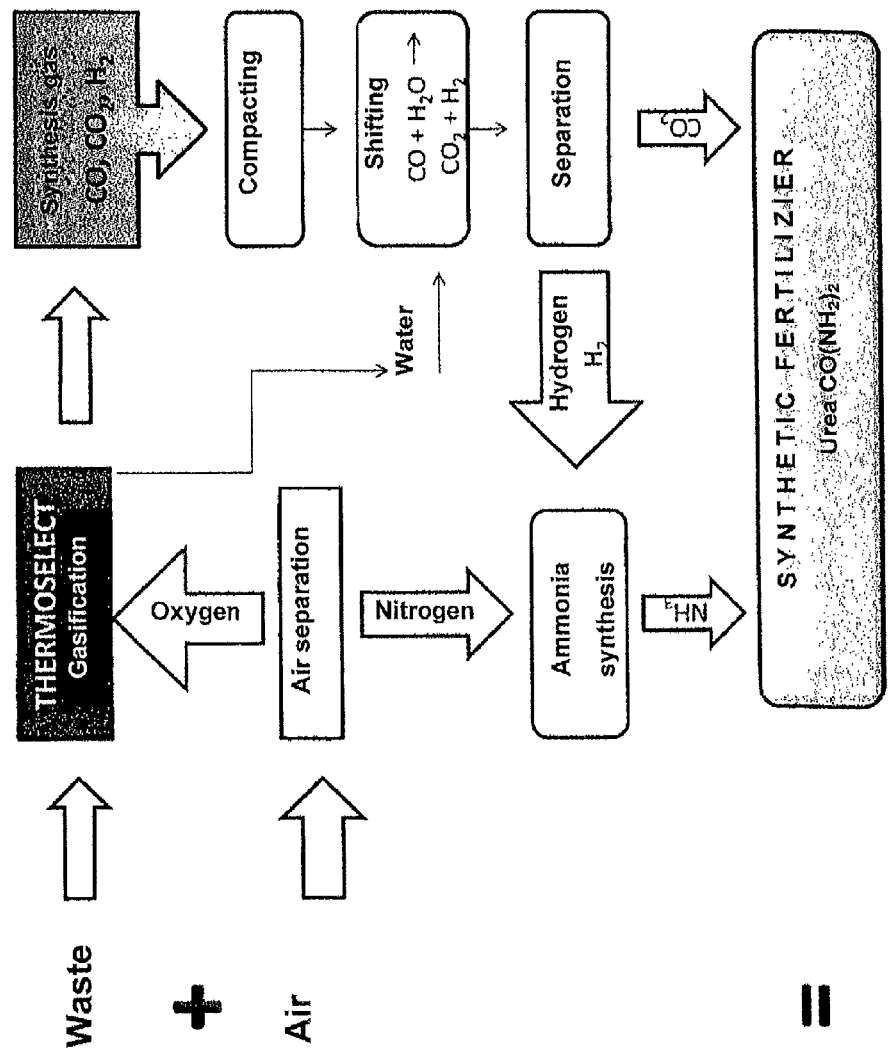

METHOD OF MANUFACTURING UREA FROM REFUSE, PREFERABLY DOMESTIC WASTE, OF ANY COMPOSITION

BACKGROUND OF THE INVENTION

The invention relates to a method of manufacturing urea as a nitrogen-rich synthetic fertilizer from refuse of any composition, preferably from domestic waste. The organic waste components are first turned into gas in a high-temperature reactor with oxygen ($O_2$) which has been obtained in a cryogenic air separation plant. A synthesis gas arises which predominantly comprises carbon monoxide (CO), hydrogen ($H_2$) and carbon dioxide ($CO_2$). The carbon monoxide (CO) contained in the synthesis gas is subsequently converted with steam into hydrogen ($H_2$) and carbon dioxide ($CO_2$). The hydrogen is subsequently separated and is used for ammonia synthesis together with the elementary nitrogen ($N_2$) which arises as a by-product in cryogenic air separation. In the last process step, urea ($CO(NH_2)_2$) is manufactured from ammonia ($NH_3$) and the further synthesis gas component carbon dioxide ($CO_2$).

The population of the world increased from 3 billion in 1960 to more than 7 billion in 2011. A disproportionately high growth of the world's population must also be anticipated in the next few decades, with the predominant portion of population growth currently taking place in the developing countries or in the less developed and poorer states of the world.

Since the area for agricultural use is limited and since additional usable areas can only be created in a small amount, the feeding of the world's population represents an ever increasing problem. Only if it becomes possible significantly to increase the specific yields of the available usable areas will there be a real chance also to feed the world's population in the future. It is possible to increase the specific yields of the available usable areas by an increased use of fertilizers.

Urea with a nitrogen content of 46.62% is the most important nitrogen fertilizer in the world. Urea is obtained on a large technical scale from natural gas. For this purpose, large chemical plant is used which produces urea from natural gas, air and water in the process steps hydrogen manufacture, ammonia manufacturer and urea synthesis.

Approximately 130 million metric tonnes (t) of urea were produced worldwide in 2009. The price of urea has risen by around 80% to € 350 per tonne over the last three years. The increasing natural gas prices and the rising demand for urea will have the result that the urea prices will also rise disproportionately in the future.

To be able to satisfy the increasing demand for urea as a synthetic fertilizer containing nitrogen, means and ways will have to be found to significantly increase annual urea production.

The amount of waste has also risen disproportionately with the population growth and increasing wealth and the search for a more environmentally acceptable solution of the waste problem is becoming more and more important.

An attempt is being made to solve the waste problem in a sustainable manner using thermal waste utilization technologies. The "thermoselect process" is taking up a preeminent position among these thermal processes. In the "thermoselect process", waste of the most varied composition and consistence is gasified with pure oxygen in a high-temperature reactor at a temperature of up to 2000° C. In this process, a synthesis gas arises which primarily comprises the molecules hydrogen ($H_2$), carbon monoxide (CO) and carbon dioxide ($CO_2$).

The oxygen used for gasifying the organic waste components is obtained by a cryogenic air separation process corresponding to the prior art. Elementary nitrogen arises as a by-product in this process which has previously been discharged to the atmosphere. The "thermoselect process" is described in EP 0790291 B1 and EP 0726307 B1.

SUMMARY OF THE INVENTION

It is the object of the present invention to manufacture urea inexpensively from the products and by-products at inexpensive prices which arise in the gasification of waste in accordance with the "thermoselect process", without gaseous emissions such as $CO_2$ polluting the air in so doing.

The above object is achieved by the method in accordance with the invention as it is defined in the claim.

The method in accordance with the invention comprises the following process steps:

In the first step, synthesis gas primarily comprising carbon monoxide (CO), carbon dioxide ($CO_2$) and hydrogen ($H_2$) is produced by a high-temperature gasification of the waste with pure oxygen in accordance with the "thermoselect process". It is important here that the required oxygen is obtained in accordance with the cryogenic air separation process. Elementary nitrogen arises as a by-product in this process.

In the second stage, the carbon monoxide (CO) contained in the synthesis gas is converted into carbon dioxide ($CO_2$) and hydrogen ($H_2$) by means of steam ($H_2O$). In this process step, the steam is preferably used which arises on the gasification of the waste in the high-temperature reactor.

After separation of the hydrogen ($H_2$) from the carbon dioxide ($CO_2$), the hydrogen ($H_2$) is converted into ammonia ($NH_3$) together with the nitrogen ($N_2$) which arises as a by-product in the air separation.

In the final step, urea ($CO(NH_2)_2$) is obtained from ammonia ($NH_3$) and carbon dioxide ($CO_2$) from the synthesis gas.

The main advantages of the method in accordance with the invention are that

Waste of the most varied composition is transformed completely into useful products by gasification with oxygen in accordance with the "thermoselect process" without polluting the environment, whereas in all other known thermal processes the environment is polluted by the highly toxic residual substances which have to be disposed of and by gaseous emissions such as $CO_2$; that the elementary nitrogen which arises as a by-product in the air separation, is used together with the hydrogen contained in the shifted synthesis gas for ammonia synthesis; that the ammonia obtained as an intermediate product is used together with the carbon dioxide contained in the shifted synthesis gas for the urea production; and that in the method in accordance with the invention, no gaseous emissions such as $CO_2$ pollute the environment. If more $CO_2$ should be contained in the shifted synthesis gas than is required for ammonia synthesis, ammonia can be bought in order also to utilize the excess $CO_2$ for the urea synthesis.

When the method proposed here is used, synthetic fertilizer can e.g. be obtained from urea, with around 600 kg nitrogen-rich synthetic fertilizer arising per tonne of waste. The current market price of this fertilizer is around €350 per tonne.

All the costs of the process described here, including all investment costs, can be covered without problem with a specific surplus of around €200 per tonne which can be achieved by the sale of the nitrogen-rich synthetic fertilizer. An above-average return on the capital invested is ensured independently of the amount of the fees which are recorded for the disposal of the waste.

BRIEF DESCRIPTION OF THE DRAWING

The invention will be explained in more detail in the following with reference to the drawing, in which:

FIG. 1 is a general process flowchart of a method in accordance with the invention.

DETAILED DESCRIPTION OF THE INVENTION

In this process, the waste of any desired composition is gasified in a high-temperature reactor with $O_2$ at a temperature of at least 1000° C. to 2000° C., preferably at around 1500° C. for forming the synthesis gas. The indwell time of the synthesis gas in the reactor amounts to 1.0 seconds to 5.0 seconds, preferably around 2.0 seconds. To prevent any reformation of the synthesis gas components into toxic products, the synthesis gas is subjected to a shock cooling (quenching).

In the next step, the synthesis gas which is formed by the above-described high-temperature treatment is first preferably compressed to 10 to 80 bar, preferentially to around 50 bar.

To utilize the synthesis gas as efficiently as possible for the obtaining of nitrogen-rich synthetic fertilizer, the hydrogen portion in the synthesis gas should be as high as possible. The reaction is carried out in accordance with the formula $CO+H_2O=CO_2+H_2$ with the aid of the so-called shift reaction corresponding to the prior art, preferably in a cooled reactor with a catalytic fixed bed, by metering in steam. Since heat arises due to the exothermal reaction, the reactor is cooled to the ideal temperature for the catalyst of 300° C. using water.

The shifted synthesis gas, which preferably comprises hydrogen and carbon dioxide, is stripped in a next process step—which likewise corresponds to the prior art—in that the hydrogen is separated. A residual gas remains which almost exclusively comprises carbon dioxide.

The hydrogen is used catalytically together with the nitrogen from the air separation plant in a synthesis reactor for obtaining ammonia.

In the next method step, the urea synthesis takes place in that ammonia and carbon dioxide from the residual gas are used catalytically for obtaining urea as nitrogen-rich synthetic fertilizer. If the $CO_2$ amount is larger than the $CO_2$ requirement which is necessary for urea synthesis, $NH_3$ can be bought in to use the $CO_2$ surplus for urea synthesis.

The advantage of the method described here is above all that the waste utilization does not result in any gaseous emissions. All substances which arise can be used industrially. Only the substances such as hydrogen and carbon dioxide obtained from the gasification of organic waste components in accordance with the "thermoselect process" are used for the obtaining of nitrogen-rich synthetic fertilizer. The elementary nitrogen required for the ammonia synthesis arises as a by-product in the air separation plant.

In a modification of the method, the energy required for the method can also be obtained from regenerative energies, e.g. from photovoltaics.

The invention claimed is:

1. A method for the manufacture of urea ($CO(NH_2)_2$), characterized in that urea is manufactured from municipal solid waste of any composition without producing any gaseous emissions, comprising the following steps:

a) generation of a synthesis gas (CO, $CO_2$ and $H_2$) by compression and at least partial pyrolysis of municipal solid waste, subsequent feeding of the pyrolyzed solid municipal waste in still compressed form in a reactor, wherein the pyrolized municipal solid waste forms a gasification bed in the reactor, and also subsequent high-temperature treatment of the pyrolized municipal solid waste in the reactor at a temperature of at least 1000° C. to 2000° C. with $O_2$ which is produced by means of a cryogenic air separation process, in which the indwell time of the synthesis gas in the reactor is 1.0 to 5.0 seconds;

b) conversion of the CO contained in the synthesis gas using $H_2O$ into $CO_2+H_2$ (water shift reaction) and separation of the $CO_2$ from the $H_2$;

c) conversion of the $H_2$ obtained from step b) using $N_2$ which originates from the cryogenic air separation from step a) for forming ammonia ($NH_3$); and d) conversion of the $NH_3$ from step c) using $CO_2$ from step b) for forming urea ($CO(NH_2)_2$).

* * * * *